United States Patent [19]

Wunder et al.

[11] 4,247,731

[45] Jan. 27, 1981

[54] PROCESS FOR THE MANUFACTURE OF LOWER ALKENES FROM METHANOL AND/OR DIMETHYL ETHER

[75] Inventors: Friedrich Wunder, Flörsheim am Main; Hans-Jürgen Arpe, Kelkheim; Horst Hachenberg, Walluf; Ernst I. Leupold, Neu-Anspach, all of Fed. Rep. of Germany

[73] Assignee: Hoechst Aktiengesellschaft, Frankfurt, Fed. Rep. of Germany

[21] Appl. No.: 75,983

[22] Filed: Sep. 17, 1979

Related U.S. Application Data

[63] Continuation of Ser. No. 967,375, Dec. 7, 1978, abandoned.

[30] Foreign Application Priority Data

Dec. 10, 1977 [DE] Fed. Rep. of Germany ....... 2755229

[51] Int. Cl.$^3$ .............................................. C07C 1/00
[52] U.S. Cl. ................................................... 585/640
[58] Field of Search ........................................ 585/640

[56] References Cited

U.S. PATENT DOCUMENTS

| | | | |
|---|---|---|---|
| 3,529,033 | 9/1970 | Frilette et al. | 585/640 |
| 4,079,096 | 3/1978 | Givens et al. | 585/640 |
| 4,148,836 | 4/1979 | Chen et al. | 585/640 |

*Primary Examiner*—John F. Niebling
*Attorney, Agent, or Firm*—Curtis, Morris & Safford

[57] ABSTRACT

Lower alkenes, especially ethylene, are produced from methanol and/or dimethyl ether in the presence of aluminum silicate catalysts containing manganese and possibly further co-catalysts.

6 Claims, No Drawings

PROCESS FOR THE MANUFACTURE OF LOWER ALKENES FROM METHANOL AND/OR DIMETHYL ETHER

This is a continuation of application Ser. No. 967,375 filed Dec. 7, 1978, abandoned.

It is known to react methanol and/or dimethyl ether at temperatures above about 260° C. under a total pressure of from 0.5 to about 100 bars on specific molecular sieves (zeolites) to obtain a mixture of different alkanes, alkenes and aromatic compounds. According to DE-OS No. 2,615,150 it is necessary, for example, not only to select the molecular sieve with respect to numerous physical and chemical criteria, but also to take some special measures—which, however, impair the efficiency—such as reduction of the conversion, reduction of the methanol/dimethyl ether partial pressure, dilution of the molecular sieve with inert carrier material, in order to obtain a useful selectivity. In spite of all, a considerable proportion of aromatic compounds is generally formed.

It is also known to modify molecular sieves with phosphorus compounds, for example with trimethyl phosphite as disclosed in U.S. Pat. No. 3,911,041, whereby the selectivity of the methanol/dimethyl ether reaction is improved with respect to the alkene formation. The production of the molecular sieves modified with phosphorus is rather complicated, anhydrous conditions are required and expensive phosphorus compounds must be used. Moreover, the molecular sieve catalysts have relatively short service life, they must be regenerated approximately every three weeks. Finally, the selectivity of olefins obtainable with modified molecular sieves of this type is still unsatisfactory, considerable proportions of saturated and aromatic hydrocarbons are still formed.

It is, therefore, the object of the present invention to modify the reaction of methanol and/or dimethyl ether in such a way that the industrially important lower alkenes, for example ethylene, propene and butenes, preferably ethylene, are obtained in a high selectivity with a high conversion rate of methanol and/or dimethyl ether. The process of the invention for the manufacture of lower alkenes comprises the reaction of methanol and/or dimethyl ether in the presence of aluminum silicate catalysts containing from 0.1 to 10% by weight of manganese calculated on the aluminum silicate.

To obtain a high selectivity it proved advantageous in many cases to use further elements as co-catalysts besides manganese. Elements of this type are those which are mono-, bi- or trivalent in their compounds, for example the alkali metals (preferably lithium, sodium and potassium), the alkaline earth metals (preferably magnesium and calcium), zinc, lanthanum, rare earth (such as praseodymium, neodymium, samarium gadolinium or mixtures thereof, for example didymium) and beryllium. As co-catalyst magnesium is especially preferred. Co-catalysts of the invention are elements of the first or second main group, or the second or third sub-group of the Periodic Table. The mode of action of manganese in combination with an aluminum silicate in the reaction of methanol and/or dimethyl ether to obtain lower alkenes is surprising since so far only phosphorus and nitrogen compounds proved to be suitable for the modification of molecular sieves to be used for a selective conversion of this type.

In the process of the invention aliphatic and aromatic hydrocarbons boiling in the range of gasoline or there above are not formed or formed in a negligible amount only.

The presence of manganese in the catalysts involves a further advantage. On occasion of a regeneration, generally necessary after a long period of operation, by burning off the coke deposits with air or oxygen and steam, the redox properties of manganese facilitate the oxidation process, so that the regeneration can be carried out under mild conditions without substantial influence on the catalyst structure. The term "under mild conditions" means that the regeneration proceeds faster at the temperatures of the state of the art or that it can be performed at temperatures that are lower than those used according to the state of the art.

Suitable aluminum silicates are, for example, the usual, amorphous, acidic cracking catalysts generally containing about 13 to 25% by weight of aluminum oxide and 75 to 87% by weight of silicon oxide. Natural or synthetic, crystalline aluminum silicates can also be used, for example faujasites, zeolites, chabasites, analcite, gismondite, gmelinite, natrolite, mordenites and erionites, or in general, the so-called molecular sieves.

In the case of crystalline molecular sieves with varying pore diameters it proved advantageous to use those having large pores, for example having a diameter of 5 Å and there above.

To produce the catalyst according to the invention 0.1 to 10% by weight of manganese are applied to the aluminum silicate in the form of manganese salt solutions. To this end, the aluminum silicate can be impregnated with a solution of manganese salts and then dried. Suitable solvents are preferably water, methanol, formamide, dimethyl formamide or mixtures thereof, water being generally preferred. To apply the manganese it is likewise possible to allow the manganese salt solution to act on the aluminum silicate for a prolonged period of time, to wash the catalyst with pure solvent and then to dry it.

When molecular sieves are used, they can be impregnated by a method generally used for these materials, for example by exchange of cations present on the molecular sieve for manganese, or by intermediate transformation of the molecular sieve into the proton form with subsequent treatment with the solution of a manganese salt.

The other metal salts having a co-catalytic activity can be applied together with the manganese salt, for example by mixing the solution of the manganese salt with a solution of one or several of the other metal salts and impregnating the catalyst with the mixture obtained. Alternatively, they can be applied successively to the aluminum silicate.

Suitable manganese salts are all soluble salts such as the chloride, sulfate, nitrate, formate, acetate, propionate, butyrate, lactate, citrate, tartrate, and salts of malic acid. The co-catalysts can also be used in the form of these salts. If common solutions of manganese and the co-catalytically active element are used, the mutual influence on the solubility has to be taken into consideration, that is to say with the use of calcium or barium it is unsuitable to use sulfate as anion.

With the use of natural, crystalline aluminum silicates it is often recommendable to wash the catalyst with water prior to its impregnation with the manganese and cocatalyst salts in order to prevent the metal from being precipitated in the form of their hydrated oxides.

After impregnation, the catalysts are dried at atmospheric pressure, reduced pressure or elevated pressure at room temperature or elevated temperatures. In general, drying is performed at temperatures below 600° C., preferably in the range of from 100° to 200° C.

When methanol is used as starting material, it can be passed directly over the catalyst or it can be first transformed into dimethyl ether in a series-connected dehydration reaction in the presence of a conventional dehydration catalyst, such as aluminum oxide or aluminum silicate, and the dimethyl ether is then passed over the catalyst according to the invention. Though the latter mode of reaction necessitates two stages, it is sometimes advantageous to remove in a preliminary stage part of the water to be separated in the total reaction.

Alternatively, mixtures of methanol and dimethyl ether or dimethyl ether alone can be used as starting material.

The starting components methanol and/or dimethyl ether can be diluted for the reaction with inert gases. To lower the partial pressure there may be used, for example, nitrogen, carbon dioxide, alkenes or even water. The reaction can then be carried out under reduced pressure down to 0.1 bar.

It is preferred, however, to carry out the reaction under a pressure in the range of from 1 to 100 bars, more preferably 1 to 50 bars.

In general, the reaction temperature is in the range of from 300° to 500° C., preferably 350° to 450° C. and more preferably 380° to 420° C. When the reaction conditions are chosen in a manner such that the conversion of methanol and/or dimethyl ether is incomplete, the unreacted proportions can be separated and recycled.

The alkenes produced by the process of the invention can be separated by conventional methods, for example by distillation, from the alkanes formed as by-products and from one another.

The process of the invention makes it possible to produce industrially important lower alkenes from methanol and/or dimethyl ether in a particularly selective and thus economical manner. The catalyst to be used according to the invention can be prepared in a surprisingly simple manner from readily accessible substances.

The following Examples illustrate the invention.

EXAMPLE 1

100 ml of a commercial molecular sieve with the designation 13x (empirical formula $(Na_{86}(Al_2O_3)_{86}(SiO_2)_{106}.276H_2O$, diameter of pore openings 10 Å, water absorption capacity 36%, zeolite lattice structure) are washed with water at 25° C. until the supernatant water has reached a pH of 7.3. The wet molecular sieve is added to 100 ml of saturated aqueous manganese acetate solution, the whole is left to stand for 48 hours, then the sieve is washed with water and dried at 120° C. The catalyst obtained contains 4.4% by weight of manganese. Over the catalyst there are passed 7 normal liters (Nl) of dimethyl ether per hour at atmospheric pressure and 380° C. With a conversion rate of 54.9%, 3.3 l of a mixture are obtained containing 31.6% by weight of ethylene
29.1% by weight of propylene
11.3% by weight of butenes
16.6% by weight of methane
3.7% by weight of ethane
1.6% by weight of propane
6.1% by weight of butane.

Thus saturated and unsaturated $C_2$-$C_4$-hydrocarbons are formed with a total selectivity of 83.4%. The selectivity for ethylene is 31.6%, for propylene 29.1% and for butenes 11.3%.

EXAMPLE 2

200 ml of a 13x molecular sieve in elongated e.g. extruded form (characteristics cf. Example 1) are washed with water in a tube having a diameter of 2.5 cm until the supernatant water has reached a pH of 7.0. Next, 400 ml of a saturated aqueous solution of magnesium propionate and manganese butyrate are passed through the tube over a period of 24 hours and the excess amount of manganese and magnesium salt is then washed out with water. After drying at 150° C., 27.5 g/h of methanol are passed over the catalyst at 400° C. and 1 bar. With a conversion rate of 90.1% there are obtained 11 g/h of water, 13 g/h of dimethyl ether and 2.57 Ni/h of a hydrocarbon mixture consisting of 46.9% by weight of ethylene
29.2% by weight of propylene
5.3% by weight of butenes
12.3% by weight of methane
3.7% by weight of ethane
0.5% by weight of propane
2.1% by weight of butane.

In view of the fact that the dimethyl ether formed can be recycled, the selectivity is 46.9% for ethylene, 29.2% for propylene and 5.3% for butene, i.e. the three olefins are formed with a total selectivity of 81.5%.

COMPARATIVE EXAMPLE 1

The catalyst is prepared under the conditions specified in Example 2 with the exception that a saturated solution containing magnesium propionate only and no manganese butyrate is used. 27.5 g/h of methanol are passed at 1 bar and 400° C. over 200 ml of the 13x molecular sieve treated in this manner. The off-gas contains 0.1% by volume of ethylene, the rest being dimethyl ether. When the temperature is raised to 500° C., the ethylene content increases to 1.3% and at 600° C. it drops again below 0.1%.

COMPARATIVE EXAMPLE 2

27.5 g/h of methanol are passed at 1 bar and 400° C. over 200 ml of a 13x molecular sieve as specified in Example 1 which has, however, not been subjected to any pre-treatment. The off-gas does not contain any ethylene, it consists almost exclusively of dimethyl ether and traces of carbon monoxide and hydrogen.

COMPARATIVE EXAMPLE 3

The reaction is carried out as described in Comparative Example 2 with the exception that prior to its use the 13x molecular sieve is washed with water until the wash water is neutral. The off-gas has the same composition as in Comparative Example 2.

EXAMPLE 3

200 g (500 ml) of a commercial amorphous aluminum silicate (25% by weight of $Al_2O_3$, 74.5% by weight of $SiO_2$, 0.05% by weight of Na, 0.03% by weight of Fe, 0.03% by weight of Ca, BET surface 325 $m^2/g$, pore volume 0.45 ml/g) are treated (according to the pore volume) with a solution consisting of 23.2 g of manganese formate and 77 ml of water, and dried at 120° C.

46 g/h of methanol are passed over the catalyst at 380° C. and 0.5 bar. 13.5 Nl of off-gas are obtained per hour consisting of 18.0% by weight of ethylene
19.9% by weight of propylene
12.2% by weight of butenes
11.6% by weight of methane
2.0% by weight of ethane
1.1% by weight of propane
23.2% by weight of butane
0.6% by weight of carbon monoxide
0.04% by weight of hydrogen
11.4% by weight of dimethyl ether 26 g of water of condensation containing 13.3% by weight of methanol are also obtained, corresponding to a conversion of 92.5% and a selectivity for saturated and unsaturated hydrocarbons of 13.1% for $C_1$
22.7% for $C_2$
23.75 for $C_3$ and
40.0% for $C_4$ provided that unreacted methanol and dimethyl ether formed are recycled. The $C_2$-$C_4$-hydrocarbons (saturated and unsaturated) are formed with a selectivity of 86.4% altogether, the selectivity for $C_2$-$C_4$-olefins being 58.3%.

EXAMPLE 4

200 g/h of methanol are passed at 500° C. and 15 bars over 300 ml of a commercial aluminum silicate catalyst (low pore diameter; 15.4% by weight of $Al_2O_3$, 0.028% by weight of $Fe_2O_3$, 0.007% by weight of $Na_2O$, 84.5% by weight of $SiO_2$, BET surface 485 m$^2$/g, pore volume 0.55 ml/g), which has been treated with a 20% aqueous manganese acetate solution and contains 1.3% of manganese. The reaction product obtained contains 8.3% by weight of methanol
1.6% by weight of dimethyl ether
14.1% by weight of ethylene
18.2% by weight of propylene
5.0% by weight of butenes
1.9% by weight of methane
50.9% by weight of water.

The conversion rate of methanol is 91.7%, the selectivity for hydrocarbons (saturated and unsaturated) is 89.4%, for ethylene it is 35.0%, for propylene 45.6% and for butenes 12.5%. The $C_2$-$C_4$-olefins together are formed with a selectivity of 93.1%.

EXAMPLE 5

50 ml of a commercial molecular sieve catalyst (commercial name AGZ 50; 30% by weight of $Al_2O_3$, 2.57% by weight of rare earths oxides, 0.49% by weight of $SO_4^=$, 0.29% by weight of $Na_2O$, 66.6% by weight of $SiO_2$, BET surface after 3 hours heating to 1000° F. = 290 m$^2$/g, pore volume 0.43 ml/g, average bulk density ABD 0.6 g /ml, average particle size APS 68$\mu$) are stirred for 10 hours with a saturated aqueous solution of manganese chloride and magnesium chloride, washed with water and dried at 110° C.

20 Nl of dimethyl ether are passed per hour over the catalyst at 390° C. and 1.5 bars. The reaction product contains 21.6% by weight of ethylene
19.3% by weight of propene
14.4% by weight of butenes
3.3% by weight of methane
3.8% by weight of dimethyl ether
37.6% by weight of water.

The conversion rate amounts to 96.2%, the selectivity for ethylene is 36.9%, for propylene 32.9%, for butenes 24.6%. The $C_2$-$C_4$-olefins are formed with a selectivity of 94.4% altogether.

EXAMPLE 6

600 g of a molecular sieve 13x are introduced into a vertical tube having an internal diameter of 25 mm and washed with desalted water. Carbon dioxide is added to the last portion of the wash water and washing is continued until the $CO_2$-containing wash water, after a time of contact with the molecular sieve of 5 hours, has a pH of 6.8. Next, a concentrated aqueous solution of manganese acetate and magnesium acetate (2.5 l) is passed through the tube over a period of 48 hours, whereupon the catalyst is washed with distilled water until no more manganese ions can be detected in the wash water. 2.8 l/h (2.2 kg) of methanol are passed over the catalyst at 430° C. and 25 bars.

The reaction product has the following composition:

14.3% by weight of ethylene
12.45 by weight of propene
7.2% by weight of butenes
3.3% by weight of methane
1.9% by weight of ethane
3.1% by weight of butane
55.1% by weight of water
1.2% by weight of methanol
0.8% by weight of dimethyl ether.

The methanol conversion amount to 98.8%. The selectivity for (saturated and unsaturated) hydrocarbons is 97.3%, the selectivity for ethylene = 33.3%
propene = 28.9%
butene = 16.8%
methane = 7.7%
ethane = 4.4%
butane = 7.2%

The selectivity for $C_2$-$C_4$-hydrocarbons (saturated and unsaturated) is 90.6%, the selectivity for $C_2$-$C_4$ olefins is 79.0%.

What is claimed is:

1. Process for the manufacture of lower alkenes which comprises reacting methanol and/or dimethyl ether on aluminum silicate catalysts containing from 0.1 to 10% by weight of manganese, calculated on the aluminum silicate.

2. The process of claim 1, wherein the catalyst contains in addition elements of the 1st or 2nd main group or of the 2nd or 3rd subgroup of the Periodic Table as co-catalysts.

3. The process of claim 1, wherein the catalyst contains in addition magnesium as co-catalyst.

4. The process of claim 1, wherein crystalline aluminum silicate is used as catalyst.

5. The process of claim 1, wherein the reaction pressure is from 1 to 100 bars.

6. The process of claim 1, wherein the reaction temperature is from 300° to 500°.

* * * * *